(12) United States Patent
Pasin et al.

(10) Patent No.: US 10,975,016 B2
(45) Date of Patent: Apr. 13, 2021

(54) SOLVENT COMPOUNDS FOR USE AS GLYCOL ETHER REPLACEMENTS

(71) Applicant: TBF ENVIRONMENTAL TECHNOLOGY INC., Surrey (CA)

(72) Inventors: David A. Pasin, Vancouver (CA); Joseph Mitchell Clarkson, Vancouver (CA); Laurel L. Schafer, Vancouver (CA)

( * ) Notice: Subject to any disclaimer, the term of this patent is extended or adjusted under 35 U.S.C. 154(b) by 0 days.

(21) Appl. No.: 16/652,956

(22) PCT Filed: Oct. 1, 2018

(86) PCT No.: PCT/IB2018/057614
§ 371 (c)(1),
(2) Date: Apr. 1, 2020

(87) PCT Pub. No.: WO2019/069210
PCT Pub. Date: Apr. 11, 2019

(65) Prior Publication Data
US 2020/0262780 A1    Aug. 20, 2020

Related U.S. Application Data

(60) Provisional application No. 62/566,794, filed on Oct. 2, 2017.

(51) Int. Cl.
| | | |
|---|---|---|
| C07C 69/96 | (2006.01) |
| C09D 7/20 | (2018.01) |
| C09D 7/63 | (2018.01) |
| A61K 8/37 | (2006.01) |
| A61K 47/14 | (2017.01) |
| C11D 3/43 | (2006.01) |

(52) U.S. Cl.
CPC ............... *C07C 69/96* (2013.01); *A61K 8/37* (2013.01); *A61K 47/14* (2013.01); *C09D 7/20* (2018.01); *C09D 7/63* (2018.01); *C11D 3/43* (2013.01); *A61K 2800/10* (2013.01)

(58) Field of Classification Search
CPC .. C07C 69/96; C09D 7/20; C09D 7/63; A61K 8/37; A61K 47/14; A61K 2800/10; C11D 3/43
USPC ........................................................ 558/276
See application file for complete search history.

(56) References Cited

U.S. PATENT DOCUMENTS

| | | | |
|---|---|---|---|
| 2,153,137 A | 4/1939 | Dickey et al. |
| 2,535,012 A | 12/1950 | Croxall et al. |
| 3,632,828 A | 1/1972 | Frevel et al. |
| 3,642,858 A | 2/1972 | Frevel et al. |
| 3,657,310 A | 4/1972 | Frevel et al. |
| 4,146,522 A | 3/1979 | Heckles |
| 4,181,676 A | 1/1980 | Buysch et al. |
| 4,238,206 A | 12/1980 | Hong |
| 5,164,497 A | 11/1992 | King et al. |
| 5,210,322 A | 5/1993 | King et al. |
| 5,430,170 A | 7/1995 | Urano et al. |
| 5,430,171 A | 7/1995 | Mitsuhashi et al. |
| 5,986,125 A | 11/1999 | Reuter et al. |
| 6,361,709 B1 | 3/2002 | Bauer et al. |
| 6,767,624 B2 | 7/2004 | Bronstert |
| 8,729,291 B2 | 5/2014 | Franzke et al. |
| 9,231,274 B2 | 1/2016 | Kinoshita et al. |
| 2011/0137067 A1 | 6/2011 | Franzke et al. |

FOREIGN PATENT DOCUMENTS

| | | |
|---|---|---|
| BE | 1006039 A3 | 4/1994 |
| CA | 1116835 A | 1/1980 |
| CA | 2940089 A1 | 9/2015 |
| CN | 101096339 A | 1/2008 |
| EP | 478073 A2 | 4/1992 |
| EP | 2283085 B1 | 2/2013 |
| GB | 1369716 | 10/1974 |
| GB | 2110234 A | 6/1983 |
| JP | 56143221 A | 11/1981 |
| JP | 2002237328 A | 8/2002 |
| JP | 2002373702 A | 12/2002 |
| JP | 201140311 A | 2/2011 |
| WO | 2004074920 A1 | 9/2004 |
| WO | 2009147469 A1 | 12/2009 |
| WO | 2015069854 A1 | 5/2015 |
| WO | 2015135701 A1 | 9/2015 |
| WO | 2016187798 A1 | 12/2016 |

OTHER PUBLICATIONS

Compounds with the following CAS Nos. 105962-62-5, 705962-61-4, 705962-60-3, 705962-59-0, 193684-73-0, 193684-72-9.
Drake, Nathan L. et al., "Some Representative Carbonates and Carbo-Ethoxy Derivatives Related to Ethylene Glycol", Journal of the American Chemical Society, 1930, vol. 52, p. 3723 (http://scihub.bz/doi/10.1021/ja01372a046).
International Search Report of corresponding PCT/IB2018/057614, dated Jan. 18, 2019, 4 pages.
Written Opinion of International Searching Authority of corresponding PCT/IB2018/057614, dated Jan. 18, 2019, 5 pages.
International Search Report of PCT/IB2018/057613, dated Feb. 5, 2019, 3 pages.
Written Opinion of International Searching Authority of PCT/IB2018/057613, dated Feb. 5, 2019, 5 pages.

*Primary Examiner* — Kristin A Vajda
(74) *Attorney, Agent, or Firm* — Lewis Roca Rothgerber Christie LLP

(57) ABSTRACT

The present disclosure provides, in part, a solvent compound for use as a substitute for a glycol ether, an alkyl ether of diethylene glycol, ethylene glycol or propylene glycol.

19 Claims, 8 Drawing Sheets

SOLVENT COMPOUNDS FOR USE AS GLYCOL ETHER REPLACEMENTS

CROSS-REFERENCE TO RELATED APPLICATION(S)

This application is a National Phase Patent Application and claims priority to and the benefit of International Application Number PCT/IB2018/057614, filed on Oct. 1, 2018, which claims priority to and the benefit of U.S. Provisional Patent Application No. 62/566,794, filed on Oct. 2, 2017, the entire contents of all of which are incorporated herein by reference.

FIELD OF INVENTION

The present disclosure relates generally to solvent compounds for use as glycol ether replacements. More specifically, the present disclosure relates to VOC-exempt solvent compounds for use as glycol ether replacements.

BACKGROUND OF THE INVENTION

Smog is known to have negative health effects on humans and the environment. A major contributor to smog formation is the release of volatile organic compounds (VOCs) which are emitted from many sources including automobile exhaust and organic solvents. VOCs are defined as "any compound of carbon, excluding carbon monoxide, carbon dioxide, carbonic acid, metallic carbides or carbonates, and ammonium carbonate, which participates in atmospheric photochemical reactions". Numerous consumer products contain VOCs as an integral component of the consumer product's function or application, such as paints or chemical coating strippers. To combat the adverse effects VOCs have on air quality in North America, agencies such as Environment and Climate Change (Canada) and the Environmental Protection Agency (United States) enforce limits on VOC content in manufacturing workplaces and consumer products. VOC emission limits in some municipalities have become even more stringent than federal standards. For example, the South Coast Air Quality Management District (SCAQMD), which regulates VOC emissions in and around Orange County, California, has found success in reducing smog levels by half since the 1980's despite population growth in the area. Such successes inspire increased awareness and provide support for SCAQMD's mission. While increased awareness and enforcing limits on VOC content has helped combat smog formation significantly, many sources of VOC emissions have not been curtailed. Replacing solvents that are known to contribute heavily to smog formation, due to high VOC content, with solvents that have zero or low VOC content are thus highly sought after. To further the health and safety of their constituents some agencies have also reviewed the toxicity of commonly used chemicals. In Canada, the use of solvents and paints alone corresponds to 15% of all VOC emissions, with 314.0 kilotonnes in 2014, making it the second largest contributor next to the oil and gas industry (734.1 kilotonnes in 2014). Since the VOC's used in paints and coatings are released into the environment, they should be as biodegradable and non-toxic as possible. Although some zero or low VOC solvents exist in the market place, their cost and limited applicability reduce their wide-spread use.

SUMMARY OF THE INVENTION

In one aspect, the present invention provides a compound of Formula (I):

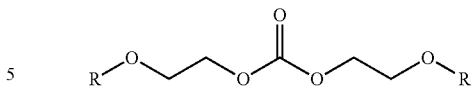

Formula (I)

where R is $C_{1-12}$ alkyl, optionally substituted from one up to the maximum number of substituents with oxygen, for use as a substitute for a glycol ether, an alkyl ether of diethylene glycol, ethylene glycol or propylene glycol.

In some embodiments, the compound may be for use as a substitute for a glycol ether or a propylene glycol.

In some embodiments, the compound may be:

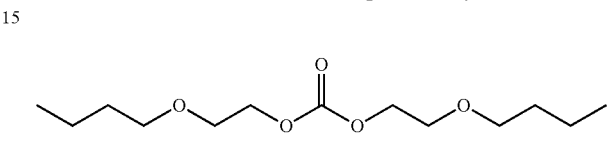

or may be

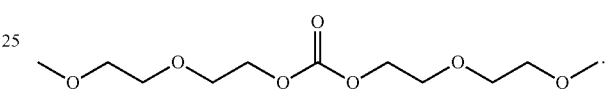

In some embodiments, the compound may be a component in a paint, coating or oil dispersant.

In some embodiments, the compound may be an excipient in a pharmaceutical, nutritional, dietary or cosmetic product.

In some embodiments, the compound may be a carrier of an active ingredient.

In some embodiments, the compound may be a component in a cleaning solvent, a reactive solvent, co-solvent, dispersant, wetting agent, coupling agent, stabilizer, chemical intermediate, coalescent or viscosity reduction solvent.

In some embodiments, the compound may be a coupling agent.

In some embodiments, the compound may be a solvent, co-solvent or coalescent in a water borne alkyd, conventional lacquer, dye, stain, latex, acrylic, alkyd, architectural paint and/or coatings formulation.

In some embodiments, the compound may be a component in a cleaning and/or degreasing formulation, in combination with a surfactant.

In some embodiments, the compound may be a chemical intermediate.

In some aspects, the present invention provides a kit or commercial package including a compound as described herein, together with instructions for use.

Other aspects and features of the present disclosure will become apparent to those ordinarily skilled in the art upon review of the following description of specific examples.

BRIEF DESCRIPTION OF THE DRAWINGS

These and other features of the invention will become more apparent from the following description in which reference is made to the appended drawings wherein.

DETAILED DESCRIPTION

Figure 1A:
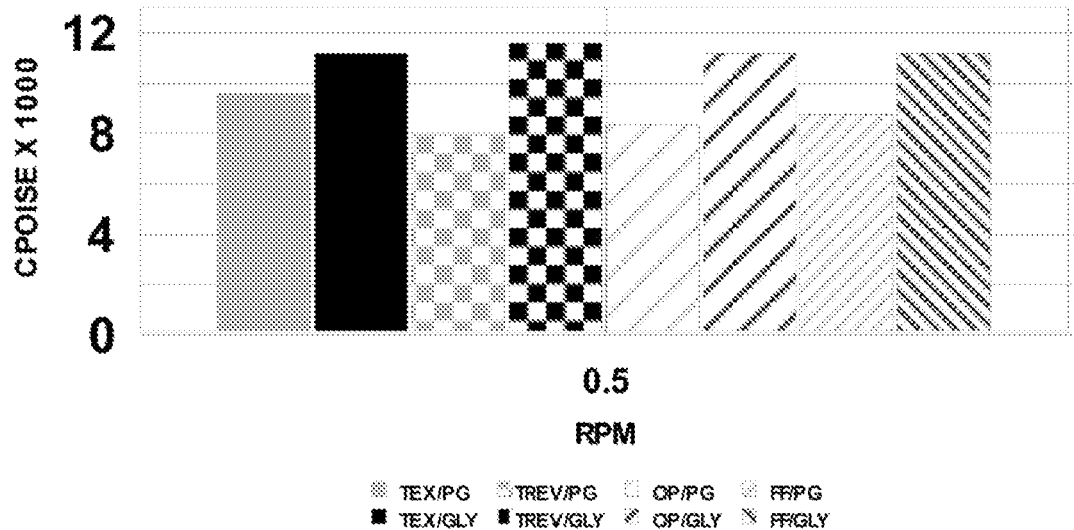
FIG. 1A is a bar graph showing the viscosity at 0.5 rpm, #4 spindle, in a PVA Flat formula.

The present disclosure provides, in part, compounds useful as substitutes for glycol ethers.

In some embodiments, the present disclosure provides a compound of Formula (I).

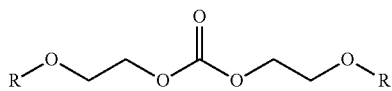

Formula (I)

where R is R is $C_{1-12}$ alkyl, for use as described herein. The compound may be:

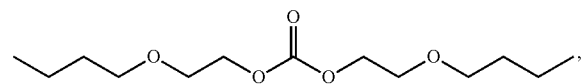 [SMILES: CCCCOCCOC(=O)OCCOCCCC]

bis(2-ButoxyEthyl Carbonate) CAS #70553-78-5 (referred to herein as GlykoSol or XBC4), or may be:

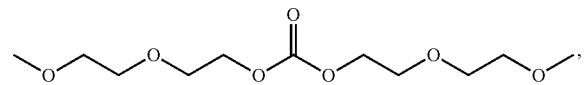

2-(hydroxymethyl)-2-[[5-(hydroxymethyl)-1,3-dioxan-5-yl]methoxymethyl]propane-1,3-diol, CAS #29536-36-5 (referred to herein as XBCA2).

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, 10, 11 or 12 carbon atoms, and which is attached to the rest of the molecule by a single bond. Unless stated otherwise specifically in the specification, the alkyl group may be optionally substituted by one or more oxygen atoms. Unless stated otherwise specifically herein, it is understood that the substitution can occur on any carbon of the alkyl group.

In some embodiments, a compound according to the present disclosure may have a high boiling point, for example, a boiling point over 200° C. In some embodiments, a compound according to the present disclosure may have a boiling point between about 200° C. to about 400° C., or any value therebetween.

In some embodiments, a compound according to the present disclosure may have very low vapour pressure, for example, a vapour pressure below 0.01 Pa. In some embodiments, a compound according to the present disclosure may have a vapour pressure between about 0.01 Pa to about 0.06 Pa, or any value therebetween.

In some embodiments, a compound according to the present disclosure may be a chemically stable solvent, for example, the compound may be stable when exposed to one or more of a variety of conditions including, without limitation: temperatures above 150° C.; water; ambient atmosphere; light; reduced pressure, etc. By "chemically stable" is meant that the compound does not exhibit substantial decomposition i.e., less than about 30% decomposition when exposed to one or more of a variety of conditions. In some embodiments, a compound according to the present disclosure may exhibit about 0% to about 30% decomposition, or any value therebetween, when exposed to one or more of a variety of conditions.

In some embodiments, a compound according to the present disclosure may not be classified as hazardous air pollutants (HAPs), or as containing Saturates, Asphaltenes, Resins and Aromatics (SARA). In some embodiments, a compound according to the present disclosure may be VOC-exempt. In some embodiments, a compound according to the present disclosure may reduce the overall VOC of a composition in which it is present. For example, when a compound according to the present disclosure is provided in combination with a VOC-containing compound, the overall VOC of the combination may be reduced. By "about" is meant a variance (plus or minus) from a value or range of 5% or less, for example, 0.5%, 1%, 1.5%, 2.0%, 2.5%, 3.0%, 3.5%, 4.0%, 4.5%, 5.0%, etc.

In some embodiments, a compound according to the present disclosure may have low toxicity as determined, for example by one or more of oral $LD_{50}$ on rats, biodegradability, teratogenicity, carcinogenicity and/or hepatic and renal toxicity measurements, which can be determined using standard methods. In some embodiments, a compound according to the present disclosure may contain reagents classified as non-carcinogenic. A compound according to the present disclosure may have an $LD_{50}$ of 5000 mg/kg or more.

In some embodiments, a compound according to the present disclosure may be substantially anhydrous, for example, containing less than 0.05 wt % water. In alternative embodiments, a compound according to the present disclosure may contain less than 500 ppm of water.

In some embodiments, a compound according to the present disclosure may break down into carbon dioxide and water. In some embodiments, a compound according to the present disclosure may break down into carbon dioxide and water when exposed to air at ambient room temperature. In some embodiments, a compound according to the present disclosure may break down into carbon dioxide and water when exposed to air at a temperature >−1° C.

In some embodiments, a compound according to the present disclosure may have a purity of, for example, at least 99.5%, for example, at least 99.6%, 99.7%, 99.8%, 99.9%, or 100%.

In some embodiments, a compound according to the present disclosure may have improved solvency, when tested against Butyl Alcohol. In some embodiments, a compound according to the present disclosure may be substantially miscible with polar, nonpolar and organic solvents as well as somewhat miscible in water.

In some embodiments, a compound according to the present disclosure may have a mild odor.

In some embodiments, a compound according to the present disclosure may be useful as a substitute for a variety of glycol ether solvents.

In some embodiments, a compound according to the present disclosure may be useful as a substitute for an alkyl ether of diethylene glycol, ethylene glycol or propylene glycol that may produce a glycol diether or a glycol ether acetate.

In some embodiments, a compound according to the present disclosure may be useful as a substitute for a propylene glycol in, for example, a paint, coating or oil dispersant. In some embodiments, a compound according to the present disclosure may be useful as a substitute for a propylene glycol in pharmaceutical, nutritional, dietary or cosmetic uses, for example, as a non-active enabling agent (excipient). Accordingly, in some embodiments, a compound according to the present disclosure may be used, without limitation, as a food additive, to carry flavors in a food and/or beverage, help retain taste and/or moisture in pet and/or livestock feed, act as a carrier of an active ingredient in, for example, a cough syrup and gel/or capsule. In some embodiments, a compound according to the present disclosure may be used in a personal care product such as, without limitation, a deodorant stick, sunscreen, shampoo, body lotion, face cream and/or lipstick. In some embodiments, a compound according to the present disclosure may be used as an excipient to stabilize foam in personal care and health care products. In some embodiments, a compound according to the present disclosure may be useful as a substitute for a propylene glycol in, for example, injectable, oral and/or topical pharmaceutical formulations.

In some embodiments, a compound according to the present disclosure may be useful as a substitute for a propylene glycol in industrial uses, for example, as a heat-transfer medium to, for example, protect against pressure burst and corrosion, control viscosity, and/or dissolve an active agent. In some embodiments, a compound according to the present disclosure may be useful as a substitute for a propylene glycol in a paint and/or and coating for, for example, wear and weather protection, as an aircraft de-icer, in a liquid detergent, antifreeze, and/or as a solvent in printing ink. In some embodiments, a compound according to the present disclosure may be useful as a substitute for a propylene glycol to make a formable plastic, for example, an unsaturated polyester resin which can be used, without limitation, in windmill blades, furniture, marine construction, gel coats, synthetic marble coatings, sheet molding compound and/or for heavy impact surfaces such as floors.

In some embodiments, an aerosolized form of a compound according to the present disclosure may be useful as a substitute for a propylene glycol to create a dense "smoke" without flames for use, for example, by the military, in fire-training procedures and/or in theatrical productions.

In some embodiments, an aerosolized form of a compound according to the present disclosure may be useful as a substitute for a propylene glycol in polyester fiber production.

In some embodiments, a compound according to the present disclosure may be useful as one or more of a cleaning solvent, a reactive solvent, co-solvent, dispersant, wetting agent, coupling agent, stabilizer, chemical intermediate, coalescent or viscosity reduction solvent.

In some embodiments, a compound according to the present disclosure may be useful as a coupling agent in a water-based and/or organic system.

In some embodiments, a compound according to the present disclosure may be useful as a co or coupling solvent in degreasing, grime, industrial, hard surface, soap-hydrocarbon and specialty concentrated and ready to use cleaning formulae.

In some embodiments, a compound according to the present disclosure may increase the solubility of a grease, oil, dirt and/or grime. In such embodiments, a compound according to the present disclosure may be useful in a cleaning solution.

In some embodiments, a compound according to the present disclosure may be useful as one or more of a solvent, co-solvent or coalescent in water borne alkyd, conventional lacquer, stain, latex, acrylic and alkyd, architectural paint and coatings formulae.

In some embodiments, a compound according to the present disclosure may be useful as one or more of a dye solvent in the printing, textile and leather industries, a component in freeze/thaw water borne system and fuel system ice inhibitors as well as a solvent used in insecticide and herbicides and a chemical reaction solvent.

In some embodiments, a compound according to the present disclosure may be useful as one or more of a coupling agent to stabilize immiscible ingredients in industrial metal cleaners, in vapor degreasers as well as aid in clarification of oil-water dispersions.

In addition, a compound according to the present disclosure may be useful in cleaning and/or degreasing applications, when used in combination with a surfactant, such as a low VOC surfactant.

In some embodiments, a compound according to the present disclosure may improve the gloss of a paint or coating.

In some embodiments, a compound according to the present disclosure may improve the integrity and/or durability of a paint or coating.

In some embodiments, a compound according to the present disclosure may improve the scrub resistance of a paint or coating.

In some embodiments, a compound according to the present disclosure may assist in the formation of a durable film of a paint or coating at less than $-1°$ C.

Without being bound to any particular theory, a compound according to the present disclosure may undergo a similar reaction as an alcohol with respect to its hydroxyl (—OH) functional group. In some embodiments, for example, a solvent according to the present disclosure may be useful as a chemical intermediate in, for example: a reaction with aldehydes and ketones to produce hemiacetals; with acetals carboxylic acids, carboxylic acid chlorides, anhydrides and inorganic acids to produce esters; with halogenating agents to produce alkoxy alkyl halides; with organic halides to produce ethers, such as glymes; with alkenes and alkynes to produce ethers; with halogenating agents to produce alkoxy alkyl halides; and/or with epoxides to produce polyether alcohols.

A compound according to the present disclosure may be prepared as described herein, or using techniques based on, or similar to, those known in the art, such as those referenced in U.S. Pat. Nos. 5,986,125, 4,181,676, 3,657,310, 3,642,858, or 3,632,828.

Example 1

Synthesis of Bis(2-ButoxyEthyl Carbonate) CAS #70553-78-5 (GlykoSol, XBC4)

The alcohol 2-butoxyethan-1-ol (1.0 L) was put in a 2 L round bottom flask. The flask was then charged with sodium methanolate (~1.5 g) and hexanes (~350 mL). Dimethyl carbonate (270 mL) is then added. Boiling stones (3-10) are added to prevent bumping during the reaction. A Dean Stark apparatus is attached to the round bottom flask, and 15 mL of distilled water is added to the trap, the rest of the trap volume is filled with hexanes. A condenser is attached to the top of the Dean Stark apparatus. The reaction is then heated gently until the distillate temperature is 53(±3) ° C. As the distillate condenses into the Dean Stark trap the methanol formed from the transesterification reaction separates to the bottom of the trap. The trap is refreshed when the bottom layer of the Dean stark trap is approximately half full. The reaction is monitored by taking $^1$H-NMR of the reaction mixture and is continued until the dimethyl carbonate is completely consumed and less than 5% of the unsymmetric organic carbonate intermediate is observed, the hexanes are then distilled off. The reaction was then cooled and filtered through a 1-3 cm layer of diatomaceous earth and transferred to another 2 L round bottom flask. The crude material was then distilled under vacuum and when the distillate reaches 130° C., it was collected and was the desired organic carbonate. The typical yield was 450 mL of the desired product.

The physical/chemical properties of XBC4 (GlykoSol) were determined to be as follows:

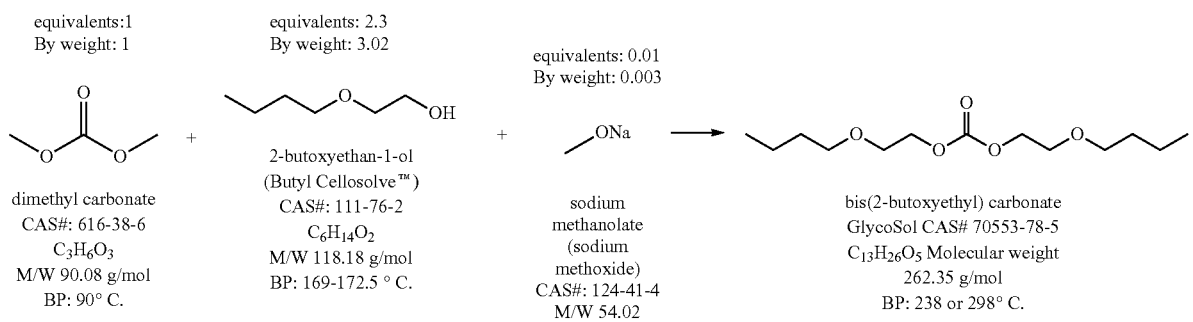

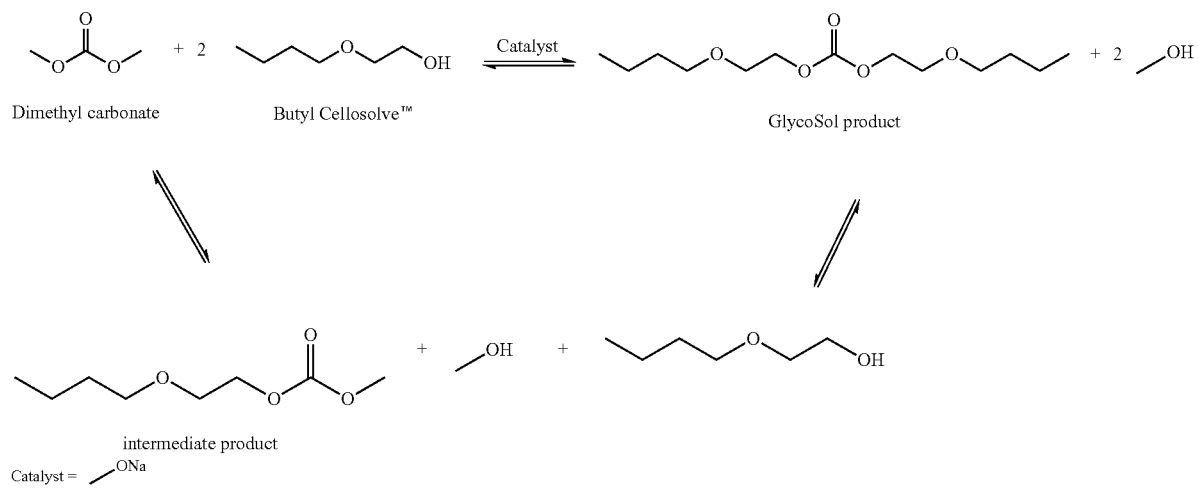

| | |
|---|---|
| Upper Explosive Limit (UEL %) | 7.31 |
| Lower Explosive Limit (LEL %) | 0.40 |
| Auto Ignition Temp (° C.) | 305 (581° F.) |
| Flashpoint (° C.) | 146.1 (295° F.) |
| Boiling Point (° C.) | 297 (566.6° F.) |
| Molecular Weight (g/mol) | 262.3 |
| Density (g/mL @ 20° C.) | 0.980 (8.22 lbs/gal) |
| Viscosity (cP @ 25° C.) | 0.60 |
| Specific Gravity (@15.5° C.) | 0.985 |
| Solubility in H$_2$O (g/mL @ 25° C.) | Partially Soluble |
| Vapour Pressure (mm Hg @ 25° C.) | 0.008 |
| Evaporation Rate (n-Butyl Acetate = 1) | 0.01 |
| Vapour Density (mm Hg Air = 1) | 0.95 |
| Freezing Point | <−60 (−76° F.) |
| Purity (Wt % Min) | 99.5% |
| Water Content (ppm) | <0.01 |
| Colour (Alpha, max) | 10 (Clear) |

-continued

| | |
|---|---|
| Volatility (%) | 100 |
| TGA Weight Loss (Range 115-240°) | 99.47% |
| Heat of Combustion (Btu/lb) | ~1200 |
| (Kcal/Kg) | ~6600 |
| (Kj/mol) | ~7300 |
| Heat of Vaporization (Btu/lb) | 63 |
| (cal/g) | 36 |
| (kj/mol) | 39 |
| Partial Coefficient (Range) | 1.9-3.0 |
| VOC (g/L) (ASTM 313-91) | 0 |

Butyl Cellosolve Solubility: Soluble
Water Solubility: Not Soluble
Odor: No Odor
Clarity: Clear XBC4 (GlykoSol) was tested in a variety of coatings and cleaning formulations, to replace different glycol ethers for use as a non-dilutive solvent or as a coalescent or a plasticizer to reduce the brittleness of the film.

4.3% of Coalescent in Acrylic Polymer (Raycryl 1001 from Specialty Polymers Tg = 36° C.)

| | XBC4 | Butyl Cellosolve | Texanol |
|---|---|---|---|
| Formula | | | |
| Raycryl 1001 (46% Solid) | 100 | 100 | 100 |
| Coalescent | 2 | 2 | 2 |
| Physical Properties | | | |
| Mixing Ease | Not Easy, Needs speed to dissolve | Easy | Not Easy, Needs speed to dissolve |
| Compatibility | Compatible | Compatible | Compatible |
| Film Clarity | Clear | Clear | Clear |
| Film Gloss | Glossy | Glossy | Glossy |
| Film Flexibility, Softness | Flexible, Soft | Brittle | Brittle |
| Film Integrity | Clear | Cracked | Cracked |

The results indicated that XBC4 (GlykoSol) works as a plasticizer and coalescent for a high Tg acrylic polymer like Raycryl 1001. XBC4 (GlykoSol) worked as a direct drop in the tests performed.

The properties of XBC4 (GlykoSol), in comparison to butyl carbitol (BC), in an acrylic polymer paint were determined to be as follows:

XBC 4 (GlykoSol) vs Butyl Carbitol (BC) in Acrylic Polymer based paint

| | Combination of Texanol and BC In Acrylic Polymer | Combination of Texanol and XBC 4 (GlykoSol) In Acrylic Polymer |
|---|---|---|
| Raw Materials | | |
| Water | 160.0 | 160.0 |
| Anionic Disperser | 2.0 | 2.0 |
| Defoamer | 8.8 | 8.8 |
| HEUR Associated Thickener | 4.4 | 4.4 |
| Titanium Dioxide | 200.0 | 200.0 |
| Calcium Carbonate | 100.0 | 100.0 |
| Water | 33.0 | 33.0 |
| Raycryl 1001 (46%) | 440.0 | 440.0 |
| Texanol | 14.0 | 14.0 |
| BC | 4.5 | — |
| XBC | — | 4.5 |
| Plasticizer | 4.0 | 4.0 |
| Silicone Defoamer | 1.0 | 1.0 |
| HEUR Associated Thickener | 3.6 | 3.6 |
| Total | 975.3 | 975.3 |
| Physical Properties | | |
| Polymer Solid % | 2.07 | 20.7 |
| Texanol on Solid Polymer % | 6.9 | 6.9 |
| BC, XBC on Solid Polymer % | 2.2 | 2.2 |
| Total Coalescent on Solid Polymer % | 9.1 | 9.1 |
| Specific Gravity g/cm3 | 1.30 | 1.30 |
| Weight Solid % | 52.2 | 52.2 |
| Volume Solid % ~ | 39.0 | 39.0 |
| VOC (Without Water) g/L | 71.8 | 58.5 |
| Test Results | | |
| Coating Properties | | |
| Viscosity | 95 KU | 95 KU |
| Fineness of Grind | 40 micron | 40 micron |
| Hide at 5.0 mils | The same | The same |
| Touch Dry @ 20° C. | 45 minutes | 50 minutes |
| Gloss @ 60 Degree | ~30 | Little More ~35 |
| Flexibility | The same | The same |

The properties of XBC4, in comparison to dipropylene glycol methyl ether (DPM), in an acrylic-modified epoxy ester-based paint were determined to be as follows:

XBC vs Dipropylene Glycol Methyl Ether (DPM) in Acrylic Modified Epoxy Ester based paint

| | DPM | XBC 4 (GlykoSol) |
|---|---|---|
| Raw Materials | | |
| Water | 155.0 | 155.0 |
| AMP 95 | 1.0 | 1.0 |
| Silicone Defoamer | 0.5 | 0.5 |
| Anionic Dispersing Agent | 3.0 | 3.0 |
| Water | 10.0 | 10.0 |
| HASE Rheology Modifier | 4.0 | 4.0 |
| Titanium Dioxide | 216.0 | 216.0 |
| Epotuf 38-698 (42.0%) | 500.0 | 500.0 |
| Cobalt Hydrocure II 5% | 0.5 | 0.5 |
| DPM | 22.0 | — |
| XBC | — | 22.0 |
| HEUR Associative Thickener | 6.3 | 6.3 |
| Sodium Nitrate 10% | 8.0 | 8.0 |
| Total | 926.3 | 926.3 |
| Physical Properties | | |
| Polymer Solid % | 22.7 | 22.7 |
| DPM, XBC Content on Solid Polymer % | 10.5 | 10.5 |
| Specific Gravity g/cm3 | 1.23 | 1.23 |
| Weight Solid % | 46.9 | 46.9 |
| Volume Solid % | 35.5 | 35.5 |
| VOC (Without Water g/L | 110 | 34 |

-continued

| XBC vs Dipropylene Glycol Methyl Ether (DPM) in Acrylic Modified Epoxy Ester based paint | | |
|---|---|---|
| | Test Results | |
| Coating Properties | DMP | XBC 4 (GlykoSol) |
| Viscosity | 90 KU | 90 KU |
| Fineness of Grind | 50 micron | 50 micron |
| Hide at 5.0 mils | The same | The same |
| Touch Dry @ 20° C. | 30 minutes | 30 minutes |
| Gloss @ 60 Degree | ~50 | ~50 |
| Flexibility | The same | The same |

Example 2

Synthesis of 2-(hydroxymethyl)-2-[[5-(hydroxymethyl)-1,3-dioxan-5-yl]methoxymethyl]propane-1,3-diol, CAS #29536-36-5 (XBCA2)

2-(hydroxymethyl)-2-[[5-(hydroxymethyl)-1,3-dioxan-5-yl]methoxymethyl]propane-1,3-diol was prepared as set forth in Example 1, herein, except 2-(2-methoxyethoxy)ethan-1-ol, CAS #111-77-3 was used in place of 2-butoxyethan-1-ol.

Example 3

Results of Bis(2-ButoxyEthyl Carbonate) CAS #70553-78-5 (GlykoSol, XBC4)

Bis(2-ButoxyEthyl Carbonate) was tested in a number of water-based flat paints, as follows. Water was added to a container and the additives were added. The container was placed under a high speed disperser and mixed under slow speed. Natrosol™ hydroxyethylcellulose was added slowly and allowed to mix for 10 minutes increasing speed as needed. The pigments were then added, slowly increasing speed and water as needed. After the pigments were added, the speed was increased to about 2800 rpms. After 10 to 15 minutes the speed was reduced to about 1000 rpms. The latex was added slowly into the vortex. The rest of the water and other additives (depending on the formulation) were then added and allowed to mix for 5 minutes.

The testing was conducted as follows. A 3 wet mil drawdown was made on a opacity chart. Dry time was done by putting the opacity chart under a Gardco Ultracycle RHT 5022 dry time tester and letting it run until the coating was dry. The optical properties were done using the same opacity chart after 24 hours dry time. The L*a*b* were read using a X-rite RM200QC. The gloss was measured using aETB-0833 glossmeter.

In some tests, bis(2-ButoxyEthyl Carbonate) was substituted for propylene glycol to evaluate its effectiveness in replacing propylene glycol to create a lower VOC and lower toxicity material. The results indicated that replacement of bis(2-ButoxyEthyl Carbonate) for propylene glycol resulted in far lower or zero (0) VOC materials. Parameters such as dry time, gloss, solids %, and opacity, which are important in measuring the qualities of a coating, were not adversely affected.

In the various tests, the following abbreviations were used:
TEX: Texanol™
PG: Propylene Glycol
GLY: GlykoSol (Bis(2-ButoxyEthyl Carbonate), XBC4)
TREV, TER or TRV: TreviSol (bis(1-butoxypropan-2-yl) carbonate)
OP: Optifilm™ 400, and
FF: Film Former IBT.

Example 4

PVA Flat Formula

Table 1 shows materials and combinations tested in a PVA flat formula.

TABLE 1

| PVA Flat Latex Formula | | | | | | | | |
|---|---|---|---|---|---|---|---|---|
| | A | B | C | D | E | F | G | H |
| WATER | | | | 397.5 | | | | |
| NATROSOL 330 PLUS | | | | 5.0 | | | | |
| KTPP | | | | 1.8 | | | | |
| COLLOIDS 226 | | | | 8.0 | | | | |
| IGEPAL CO-610 | | | | 4.0 | | | | |
| COLLOIDS 691 | | | | 3.0 | | | | |
| TIO2(R-706) | | | | 91.1 | | | | |
| HUBERCARB 325G | | | | 235.5 | | | | |
| KAMIN 70C | | | | 100.0 | | | | |
| UCAR 379 | | | | 250.0 | | | | |
| TEXANOL | 10.0 | 10.0 | | | | | | |
| OPTIFILM 400 | | | | | 10.0 | 10.0 | | |
| TREVISOL | | | 10 | 10 | | | | |
| UCAR FILM IBT | | | | | | | 10.0 | 10.0 |
| PROPYLENE GLYCOL | 23.3 | | 23.3 | | 23.3 | | 23.3 | |
| GLYKOSOL | | 23.3 | | 23.3 | | 23.3 | | 23.3 |

The results for the viscosities (PVA flat) are shown in Table 2.

TABLE 2

| | CQ217016 PVAFLAT | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 9600 | 7000 | 4240 | 3000 | 2120 | 1510 | 1016 | 774 | 1008 | 1470 | 2000 | 2840 | 4000 | 6200 | 8800 |
| TEX/GLY | 11200 | 7800 | 4880 | 3360 | 2340 | 1650 | 1056 | 760 | 1040 | 1600 | 2260 | 3160 | 4640 | 7200 | 10000 |
| TREV/PG | 8000 | 6000 | 3760 | 2600 | 1840 | 1330 | 892 | 670 | 888 | 1310 | 1800 | 2520 | 3680 | 6000 | 9200 |
| TREV/GLY | 11600 | 8400 | 5200 | 3520 | 2440 | 1710 | 1088 | 778 | 1068 | 1650 | 2320 | 3280 | 4800 | 7600 | 11200 |
| OP/PG | 8400 | 6000 | 3760 | 2640 | 1880 | 1350 | 904 | 680 | 896 | 1330 | 1820 | 2520 | 3600 | 5800 | 8800 |
| OP/GLY | 11200 | 7800 | 4960 | 3400 | 2380 | 1700 | 1116 | 820 | 1108 | 1680 | 2320 | 3240 | 4640 | 7400 | 10400 |
| FF/PG | 8800 | 6200 | 3920 | 2800 | 1980 | 1430 | 964 | 734 | 960 | 1410 | 1920 | 2680 | 3840 | 6000 | 9600 |
| FF/GLY | 11200 | 7800 | 4960 | 3400 | 2380 | 1700 | 1116 | 820 | 1108 | 1680 | 2320 | 3240 | 4640 | 7400 | 10400 |

The results for different parameters (PVA flat) are shown in Table 3.

TABLE 3

| | TEX PG CONTROL | TEX GLY | TREV PG | TREV GLY | OP PG | OP GLY | FF PG | FF GLY |
|---|---|---|---|---|---|---|---|---|
| 60 Deg Gloss | 0.7 | 1.1 | 1.3 | 1.4 | 1.4 | 1.4 | 1.6 | 1.2 |
| L* | 95.7 | 95.7 | 95.6 | 95.5 | 95.6 | 95.6 | 95.7 | 95.7 |
| a* | −0.9 | −0.9 | −0.9 | −0.9 | −0.9 | −0.9 | −0.9 | −0.9 |
| b* | 1.5 | 1.5 | 1.4 | 1.5 | 1.5 | 1.5 | 1.5 | 1.4 |
| Opacity (Y) | 88.6 | 89.3 | 88.6 | 88.8 | 87.8 | 87.8 | 88.4 | 88.1 |
| VOC (CALCULATED) (g/l) | 104.8 | 33.9 | 76.1 | 0.0 | 105.2 | 34.0 | 105.1 | 34.0 |
| DRY TIME MINUTES | 22 | 22 | 20 | 25 | 20 | 25 | 22 | 28 |
| SOLIDS (2 HRS) | 52.11% | 53.75% | 52.78% | 53.41% | 51.97% | 53.65% | 52.09% | 53.01% |
| SOLIDS (24 HRS) | 51.89% | 52.52% | 51.89% | 52.21% | 51.60% | 52.58% | 51.69% | 51.96% |
| SOLIDS CALCULATED | 51.35% | 51.41% | 51.35% | 51.41% | 51.35% | 51.41% | 51.35% | 51.41% |

Figure 1B:
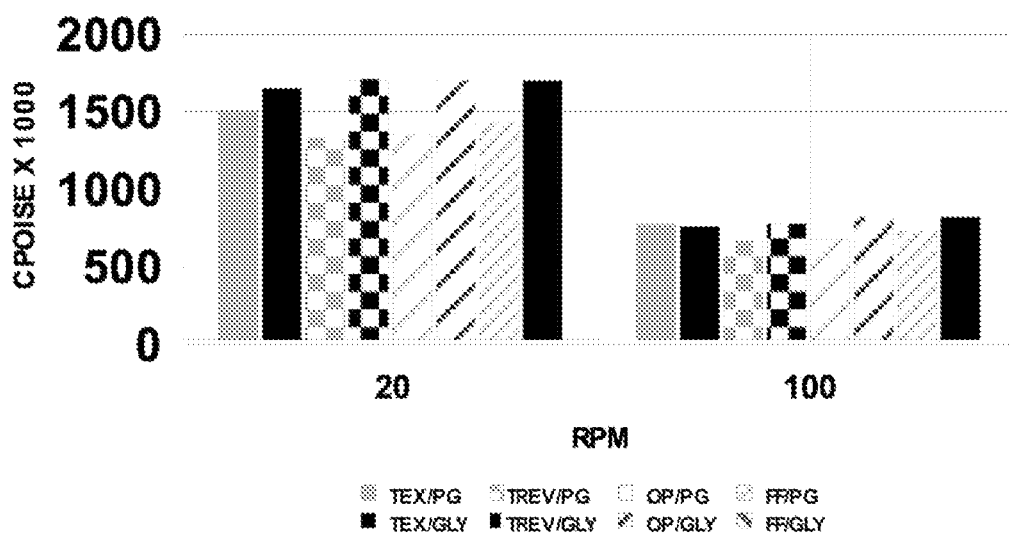
FIG. 1B is a bar graph showing the viscosity at 20 rpm and 100 rpm, #4 spindle, in a PVA Flat formula.
Figure 1C:
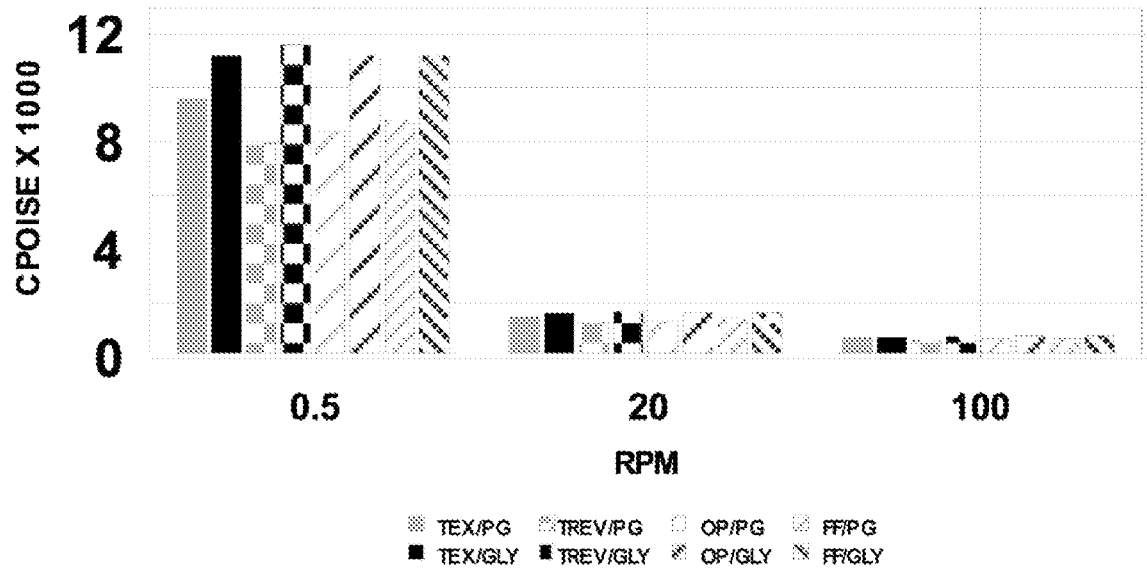
FIG. 1C is a bar graph showing the viscosity at 0.5 rpm, 20 rpm and 100 rpm, #4 spindle, in a PVA Flat formula.

FIGS. 1A-C show differences in viscosity, depending on the components. The tests were performed on a Brookfield viscometer and demonstrate that different components have different effects in thickness or viscosity within a formula.

Example 5

PVA Semi Gloss Formula

Bis(2-ButoxyEthyl Carbonate) was tested in a number of water-based flat paints, as set out in Example 3. Table 4 shows materials and combinations tested in a PVA semi gloss formula.

TABLE 4

| | A | B | C | D | E | F | G | H |
|---|---|---|---|---|---|---|---|---|
| WATER | | | | 292.0 | | | | |
| COLLOIDS 226 | | | | 6.6 | | | | |
| IGEPAL CO-630 | | | | 2.5 | | | | |
| AMP-95 | | | | 3.3 | | | | |
| COLLIDS 691 | | | | 4.9 | | | | |
| TIO2(R-706) | | | | 200.0 | | | | |
| HUBERCARB 3G | | | | 90.0 | | | | |
| NATROSOL PLUS | | | | 2.5 | | | | |
| ENCOR 379G | | | | 400.2 | | | | |
| ACRYSOL TT-935 | | | | 1.6 | | | | |
| AMMONIA | | | | 1.6 | | | | |
| TEXANOL | 14.0 | 14.0 | | | | | | |
| OPTIFILM 400 | | | | | 14.0 | 14.0 | | |
| TREVISOL | | | 14.0 | 14.0 | | | | |
| UCAR FILM IBT | | | | | | | 14.0 | 14.0 |
| PROPYLENE GLYCOL | 24.7 | | 24.7 | | 24.7 | | 24.7 | |
| GLYKOSOL | | 24.7 | | 24.7 | | 24.7 | | 24.7 |

The results for the viscosities (PVA Semi Gloss) are shown in Table 5.

TABLE 5

| CQ217015 PVA SEMIGLOSS | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 10000 | 6700 | 3760 | 2440 | 1590 | 1055 | 634 | 447 | 618 | 1005 | 1470 | 2240 | 3400 | 5800 | 8800 |
| TEX/GLY | 12400 | 8200 | 4640 | 2920 | 1910 | 1255 | 748 | 517 | 736 | 1220 | 1830 | 2780 | 4320 | 7800 | 12200 |
| TREV/PG | 7200 | 5000 | 3080 | 2040 | 1360 | 925 | 560 | 392 | 546 | 880 | 1280 | 1880 | 2840 | 4800 | 7400 |
| TREV/GLY | 12400 | 8100 | 4400 | 2740 | 1780 | 1175 | 698 | 486 | 696 | 1155 | 1730 | 2620 | 4120 | 7300 | 11800 |
| OP/PG | 7800 | 5300 | 3080 | 1980 | 1320 | 880 | 536 | 383 | 492 | 845 | 1230 | 1860 | 2720 | 4700 | 7200 |
| OP/GLY | 11400 | 7300 | 4080 | 2620 | 1700 | 1120 | 670 | 468 | 670 | 1100 | 1640 | 2480 | 3840 | 6800 | 10400 |
| FF/PG | 10400 | 6700 | 3720 | 2320 | 1530 | 1030 | 616 | 436 | 606 | 975 | 1440 | 2160 | 3320 | 5800 | 9400 |
| FF/GLY | 11400 | 7600 | 4240 | 2720 | 1780 | 1175 | 504 | 493 | 702 | 1155 | 1730 | 2620 | 4080 | 7300 | 11400 |

The results for different parameters (PVA Semi Gloss) are shown in Table 6.

TABLE 6

| | A TEX PG CONTROL | B TEX GLY | C TREV PG | D TREV GLY | E OP PG | F OP GLY | G FF PG | H FF GLY |
|---|---|---|---|---|---|---|---|---|
| 20 Deg Gloss | 4.1 | 4.0 | 3.9 | 6.2 | 5.3 | 5.5 | 3.4 | 3.4 |
| 60 Deg Gloss | 26.0 | 25.8 | 25.5 | 33.1 | 27.0 | 31.3 | 24.2 | 24.0 |
| L* | 97.0 | 96.8 | 96.8 | 96.9 | 96.4 | 96.9 | 96.7 | 96.8 |
| a* | −0.8 | −0.8 | −0.8 | −0.8 | −0.8 | −0.8 | −0.8 | −0.7 |
| b* | 0.7 | 0.8 | 0.7 | 0.8 | 0.6 | 0.8 | 0.7 | 0.7 |
| Opacity (Y) | 95.5 | 95.9 | 95.9 | 96.4 | 96.4 | 96.2 | 96.6 | 96.9 |
| DRY TIME MINUTES | 45.0 | 20.0 | 25.0 | 45.0 | 30.0 | 25.0 | 25.0 | 25.0 |
| KU VISC | 70.0 | 71.0 | 69.0 | 71.0 | 69.0 | 71.0 | 69.0 | 71.0 |
| VOC (CALCULATED) | 117.2 | 45.8 | 78.6 | 0.0 | 117.8 | 46.0 | 117.6 | 49.9 |

Figure 2A:
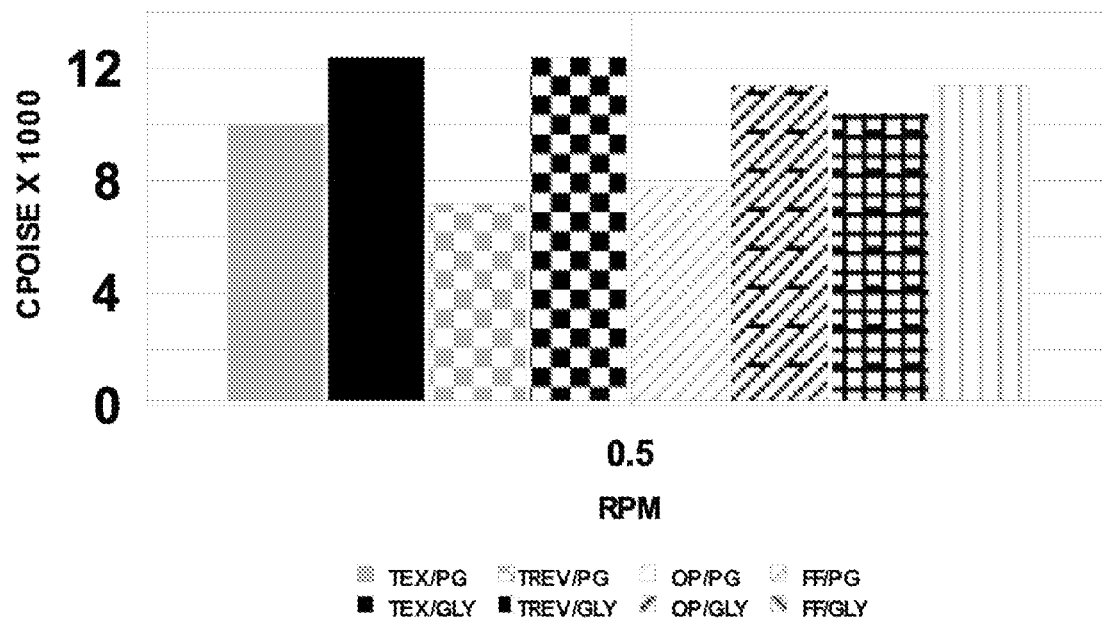
FIG. 2A is a bar graph showing the viscosity at 0.5 rpm in a PVA Semi Gloss formula.
Figure 2B:
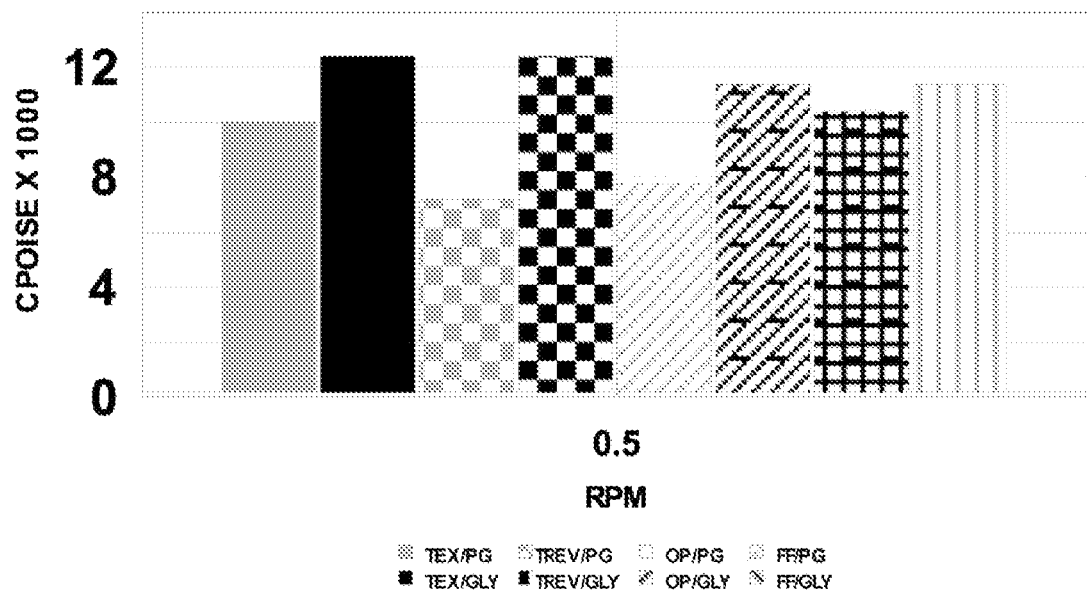
FIG. 2B is a bar graph showing the viscosity at 0.5 rpm in a PVA Semi Gloss formula.
Figure 2C:
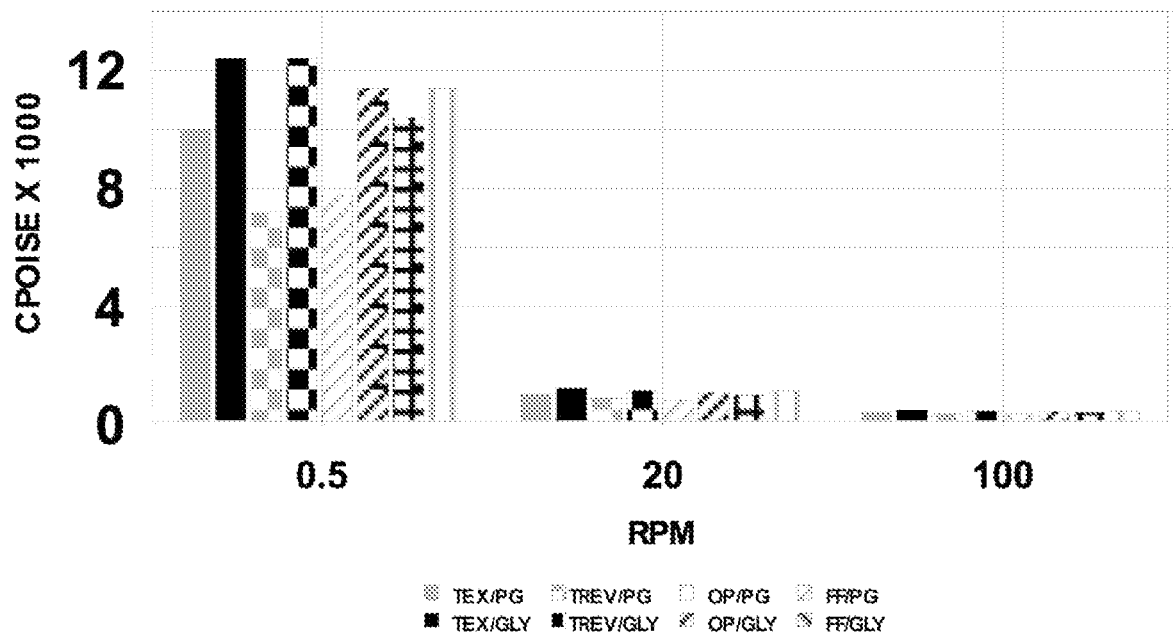
FIG. 2C is a bar graph showing the viscosity at 0.5 rpm, 20 rpm and 100 rpm in a PVA Semi Gloss formula.

FIGS. 2A-C show differences in viscosity, depending on the components. The tests were performed on a Brookfield viscometer and demonstrate that different components have different effects in thickness or viscosity within a formula.

Example 6

EVA Flat Formula

Bis(2-ButoxyEthyl Carbonate) was tested in a number of water-based flat paints, as set out in Example 3. Table 7 shows materials and combinations tested in an EVA flat formula.

TABLE 7

| | A | B | C | D | E | F | G | H |
|---|---|---|---|---|---|---|---|---|
| WATER | | | | 324.9 | | | | |
| COLLOIDS 226 | | | | 3.0 | | | | |
| IGEPAL CO-630 | | | | 2.0 | | | | |
| AMP-95 | | | | 4.5 | | | | |
| COLLIDS 691 | | | | 5.0 | | | | |
| TIO2(R-706) | | | | 150.0 | | | | |
| HUBERCARB G325 | | | | 250.0 | | | | |
| NATROSOL PLUS | | | | 6.0 | | | | |
| KAMIN 70C | | | | 150.0 | | | | |
| ECOVAE 405 | | | | 310.0 | | | | |
| TEXANOL | 5.0 | 5.0 | | | | | | |
| OPTIFILM 400 | | | | | | | 5.0 | 5.0 |
| TREVISOL | | | 5.0 | 5.0 | | | | |
| UCAR FILM IBT | | | | | | | 5.0 | 5.0 |
| PROPYLENE GLYCOL | 5.0 | | 5.0 | | 5.0 | | 5.0 | |

The results for the viscosities (EVA flat) are shown in Table 8.

TABLE 8

| CQ217023 EVA FLAT | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 46400 | 28800 | 15360 | 9680 | 6360 | 4280 | 2616 | 1892 | 2576 | 4120 | 6080 | 9200 | 14400 | 27200 | 44800 |
| TEX/GLY | 50400 | 31600 | 17120 | 10720 | 7000 | 4580 | 2896 | 2036 | 2792 | 4480 | 6680 | 10080 | 15840 | 29600 | 48800 |
| TREV/PG | 47200 | 29200 | 15520 | 9840 | 6400 | 4240 | 2536 | 1844 | 2520 | 4040 | 6000 | 9120 | 14560 | 27200 | 44800 |
| TREV/GLY | 45600 | 29200 | 15680 | 10160 | 6680 | 4460 | 2704 | 1948 | 2680 | 4300 | 6360 | 9600 | 15040 | 28400 | 47200 |
| OP/PG | 45600 | 28400 | 15200 | 9600 | 6240 | 4140 | 2528 | 1796 | 2472 | 3960 | 5840 | 8880 | 14080 | 26000 | 44000 |
| OP/GLY | 48000 | 30800 | 16640 | 10640 | 6920 | 4620 | 2824 | 1996 | 2736 | 4360 | 6440 | 9760 | 15200 | 28400 | 47200 |
| FF/PG | 48800 | 30000 | 16320 | 10320 | 6760 | 4500 | 2720 | 1952 | 2640 | 4220 | 6200 | 9440 | 14880 | 27200 | 46400 |
| FF/GLY | 52000 | 32400 | 17600 | 11200 | 7320 | 4900 | 3000 | 2116 | 2888 | 4620 | 6840 | 10400 | 16160 | 30000 | 49600 |

The results for different parameters (EVA flat) are shown in Table 9.

TABLE 9

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 0.9 | 1.4 | 1.7 | 1.8 | 1.9 | 1.9 | 1.9 | 1.9 |
| L* | 96 | 96 | 96 | 96 | 96.1 | 96.1 | 96.1 | 96.1 |
| a* | −0.7 | −0.8 | −0.7 | −0.7 | −0.7 | −0.7 | −0.7 | −0.7 |
| b* | 1.8 | 1.8 | 1.9 | 1.9 | 1.9 | 1.9 | 1.9 | 1.9 |
| Opacity (Y) | 92.2 | 92.8 | 92.2 | 92.5 | 92.5 | 92.8 | 92.5 | 92.9 |
| VOC CALCULATED | 27.6 | 14.0 | 14.0 | 0.0 | 27.6 | 14.0 | 27.6 | 14.0 |

Figure 3:
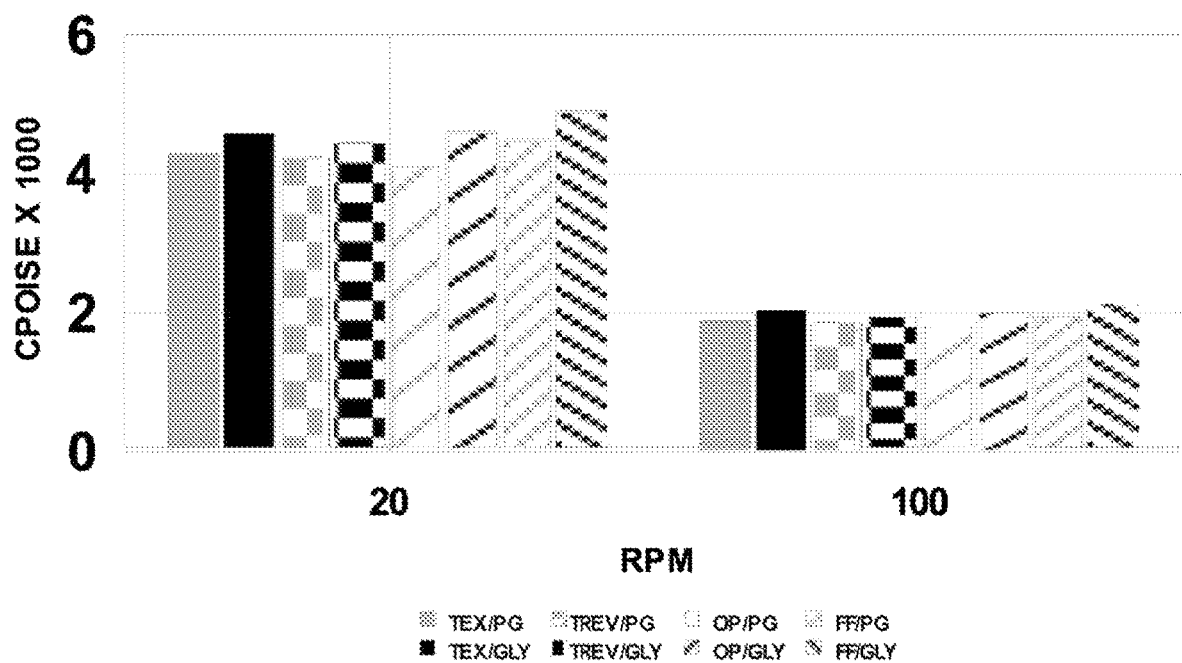
FIG. 3 is a bar graph showing the viscosity at 20 rpm and 100 rpm in an EVA Flat formula.

FIG. 3 shows the viscosity results in graphical form.

Example 7

EVA Semi Gloss Formula

Bis(2-ButoxyEthyl Carbonate) was tested in a number of water-based flat paints, as set out in Example 3. Table 10 shows materials and combinations tested in an EVA semi gloss formula.

TABLE 10

| FORMULATION EVA SEMI-GLOSS | | | | | | | |
|---|---|---|---|---|---|---|---|
|  | A | B | C | D | E | F | G | H |
| Water |  |  |  | 316.0 |  |  |  |  |
| COLLOIDS 226 |  |  |  | 3.0 |  |  |  |  |
| IGEPAL CO-630 |  |  |  | 2.0 |  |  |  |  |
| AMP-95 |  |  |  | 4.5 |  |  |  |  |
| COLLIDS 691 |  |  |  | 6.0 |  |  |  |  |
| TIO2(R-706) |  |  |  | 150.0 |  |  |  |  |
| HUBERCARB 3G |  |  |  | 80.0 |  |  |  |  |
| NATROSOL PLUS |  |  |  | 2.0 |  |  |  |  |
| ECOVAE 405 |  |  |  | 408.0 |  |  |  |  |
| ACRYSOL TT-935 |  |  |  | 8.0 |  |  |  |  |
| AMMONIA |  |  |  | 8.0 |  |  |  |  |
| TEXANOL | 5.0 | 5.0 |  |  |  |  |  |  |
| TREVISOL |  |  | 5.0 | 5.0 |  |  |  |  |
| OPTIFILM 400 |  |  |  |  | 5.0 | 5.0 |  |  |
| UCAR FILM IBT |  |  |  |  |  |  | 5.0 | 5.0 |
| PROPYLENE GLYCOL | 5.0 |  | 5.0 |  | 5.0 |  | 5.0 |  |
| GLYKOSOL |  | 5.0 |  | 5.0 |  | 5.0 |  | 5.0 |

The results for the viscosities (EVA semi gloss) are shown in Table 11.

TABLE 11

| CQ217022 EVA SEMIGLOSS | | | | | | | | | | | | | | | |
|---|---|---|---|---|---|---|---|---|---|---|---|---|---|---|---|
|  | 0.5 | 1 | 2.5 | 5 | 10 | 20 | 50 | 100 | 50 | 20 | 10 | 5 | 2.5 | 1 | 0.5 |
| TEX/PG | 21200 | 13600 | 7440 | 4760 | 3140 | 3110 | 1304 | 954 | 1284 | 2000 | 2900 | 4360 | 6720 | 12400 | 20400 |
| TEX/GLY | 22400 | 14400 | 7920 | 5160 | 3420 | 2340 | 1460 | 1038 | 1404 | 2180 | 3160 | 4720 | 7200 | 13600 | 22400 |
| TREV/PG | 20000 | 12800 | 7040 | 4560 | 3020 | 2040 | 1268 | 912 | 1224 | 1910 | 2780 | 4200 | 6480 | 12000 | 19200 |
| TREV/GLY | 22800 | 14200 | 7920 | 5080 | 3380 | 2280 | 1420 | 1018 | 1380 | 2150 | 3100 | 4640 | 7120 | 13200 | 21600 |
| OP/PG | 20400 | 13000 | 7120 | 4640 | 3060 | 2070 | 1284 | 920 | 1244 | 1940 | 2820 | 4240 | 6640 | 12200 | 20400 |
| OP/GLY | 22800 | 14400 | 8080 | 5200 | 3460 | 2330 | 1448 | 1040 | 1408 | 2190 | 3080 | 4760 | 7280 | 13600 | 21600 |
| FF/PG | 20800 | 13000 | 7200 | 4680 | 3100 | 2060 | 1292 | 938 | 1268 | 1980 | 2880 | 4360 | 6800 | 12600 | 20400 |
| FF/GLY | 21200 | 13800 | 7680 | 5040 | 3380 | 2310 | 1448 | 1046 | 1416 | 2200 | 3180 | 4760 | 7280 | 13400 | 21600 |

The results for different parameters (EVA semi gloss) are shown in Table 12.

TABLE 12

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 29.9 | 29.9 | 29.8 | 30.2 | 30.3 | 30.6 | 30.7 | 30.3 |
| L* | 96.6 | 96.5 | 96.5 | 96.4 | 96.6 | 96.6 | 96.6 | 96.5 |
| a* | −0.8 | −0.8 | −0.8 | −0.7 | −0.8 | −0.7 | −0.8 | −0.8 |
| b* | 0.9 | 1.0 | 0.9 | 1.0 | 1.0 | 1.0 | 0.9 | 1.0 |
| Opacity (Y) | 93.4 | 93.3 | 9.9 | 93.1 | 92.9 | 92.7 | 93.0 | 92.6 |
| DRY TIME MINUTES | 40 | 35 | 32 | 35 | 35 | 35 | 35 | 40 |
| VOC CALCULATED | 34.7 | 17.6 | 17.7 | 0.0 | 34.7 | 17.7 | 34.7 | 17.7 |

Example 8

Styrene Acrylic Flat Formula

Bis(2-ButoxyEthyl Carbonate) was tested in a number of water-based flat paints, as set out in Example 3. Table 13 shows materials and combinations tested in a styrene acrylic flat formula.

TABLE 13

FORMULATION STRYENE ACRYLIC FLAT

|  | A | B | C | D | E | F | G | H |
|---|---|---|---|---|---|---|---|---|
| WATER |  |  |  | 233.9 |  |  |  |  |
| COLLOIDS 226 |  |  |  | 3.0 |  |  |  |  |
| IGEPAL CO-630 |  |  |  | 2.0 |  |  |  |  |
| AMP-95 |  |  |  | 4.8 |  |  |  |  |
| COLLIDS 691 |  |  |  | 6.0 |  |  |  |  |
| NATROSOL PLUS |  |  |  | 6.0 |  |  |  |  |
| TIO2(R-706) |  |  |  | 150.0 |  |  |  |  |
| HUBERCARB 3G |  |  |  | 250.0 |  |  |  |  |
| ENCOR 471 |  |  |  | 350.0 |  |  |  |  |
| ENCOR 471 |  |  |  | 350.0 |  |  |  |  |
| TEXANOL | 30.2 | 30.2 | — | — | — | — | — | — |
| TREVISOL | — | — | 30.2 | 30.2 | — | — | — | — |
| OPTIFILM 400 | — | — | — | — | 30.2 | 30.2 | — | — |
| UCAR FILM IBT | — | — | — | — | — | — | 30.2 | 30.2 |
| PROPYLENE GLYCOL | 23.0 | — | 23.0 | — | 23.0 | — | 23.0 | — |
| GLYOKSOL | — | 23.0 | — | 23.0 | — | 23.0 | — | 23.0 |

The results for different parameters (styrene acrylic flat) are shown in Table 14.

TABLE 14

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 2.1 | 2.1 | 2.2 | 2.2 | 2.2 | 2.2 | 2.2 | 2.1 |
| L* | 96.2 | 96.3 | 96.1 | 96.4 | 96.2 | 96.3 | 96.2 | 96.2 |
| a* | −0.9 | −0.9 | −0.9 | −0.9 | −0.9 | −0.9 | −0.9 | −0.9 |
| b* | 1.6 | 1.6 | 1.5 | 1.5 | 1.5 | 1.5 | 1.5 | 1.5 |
| Opacity (Y) | 93.1 | 93.4 | 92.8 | 93.4 | 92.8 | 93.4 | 93.4 | 92.8 |
| VOC CALCULATED | 129.6 | 77.5 | 60.8 | 0.0 | 130.1 | 78.2 | 129.9 | 78.2 |
| DRY TIME MINUTES | 35 | 35 | 40 | 30 | 35 | 45 | 28 | 25 |

Figure 4:
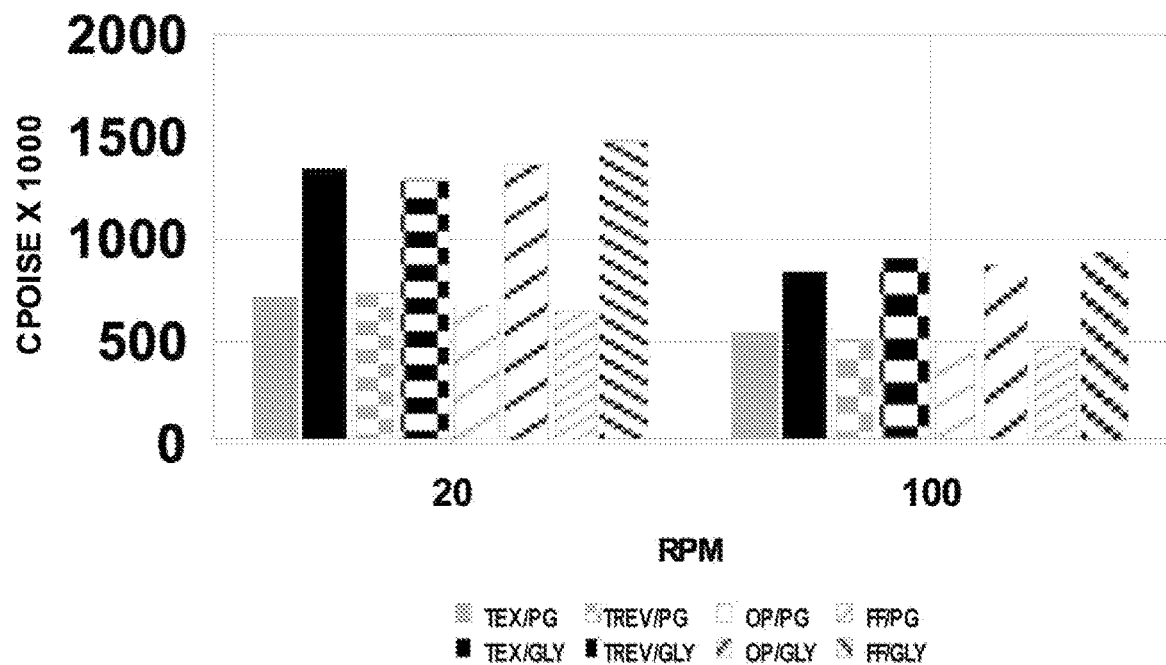
FIG. 4 is a bar graph showing the viscosity at 20 rpm and 100 rpm in a Styrene Acrylic Flat formula.

FIG. 4 shows the viscosity results (styrene acrylic flat) in graphical form.

Example 9

Styrene Acrylic Semi Gloss Formula

Bis(2-ButoxyEthyl Carbonate) was tested in a number of water-based flat paints, as set out in Example 3. Table 15 shows materials and combinations tested in a styrene acrylic semi gloss formula.

TABLE 15

FORMULATION STRYENE ACRYLIC SEMI-GLOSS

|  | A | B | C | D | E | F | G | H |
|---|---|---|---|---|---|---|---|---|
| WATER |  |  |  | 402.4 |  |  |  |  |
| COLLOIDS 226 |  |  |  | 10.7 |  |  |  |  |
| IGEPAL CO-630 |  |  |  | 4.0 |  |  |  |  |
| AMP-95 |  |  |  | 5.3 |  |  |  |  |
| COLLIDS 691 |  |  |  | 8.0 |  |  |  |  |
| NATROSOL PLUS |  |  |  | 4.0 |  |  |  |  |
| TIO2(R-706) |  |  |  | 150.6 |  |  |  |  |
| HUBERCARB 3G |  |  |  | 34.2 |  |  |  |  |
| ENCOR 471 |  |  |  | 381.1 |  |  |  |  |

TABLE 15-continued

| | FORMULATION STRYENE ACRYLIC SEMI-GLOSS | | | | | | | |
|---|---|---|---|---|---|---|---|---|
| | A | B | C | D | E | F | G | H |
| ACRYSOL TT-935 | | | | 3.3 | | | | |
| AMMONIA | | | | 2.7 | | | | |
| ENCOR 471 | | | | 381.1 | | | | |
| TEXANOL | 30.2 | 30.2 | — | — | — | — | — | — |
| TREVISOL | — | — | 30.2 | 30.2 | — | — | — | — |
| OPTIFILM 400 | — | — | — | — | 30.2 | 30.2 | — | — |
| UCAR FILM IBT | — | — | — | — | — | — | 30.2 | 30.2 |
| PROPYLENE GLYCOL | 23.0 | — | 23.0 | — | 23.0 | — | 23.0 | — |
| GLYKOSOL | — | 23.0 | — | 23.0 | — | 23.0 | — | 23.0 |

The results for different parameters (styrene acrylic semi gloss) are shown in Table 16.

TABLE 16

| | TEX PG CONTROL | TEX GLY | TREV PG | TREV GLY | OP PG | OP GLY | FF PG | FF GLY |
|---|---|---|---|---|---|---|---|---|
| 60 Deg Gloss | 6.8 | 13.7 | 6.3 | 14.9 | 5.2 | 12.5 | 6.0 | 14.0 |
| L* | 96.0 | 95.6 | 96.3 | 96.4 | 96.4 | 96.5 | 96.4 | 95.9 |
| a* | −0.8 | −0.8 | −0.8 | −0.8 | −0.8 | −0.8 | −0.8 | −0.8 |
| b* | 0.7 | 0.7 | 0.7 | 0.7 | 0.7 | 0.7 | 0.7 | 0.7 |
| Opacity (Y) | 90.2 | 90.9 | 90.1 | 90.4 | 90.8 | 90.1 | 90.5 | 90.7 |
| VOC CALCULATED | 197.2 | 121.3 | 97.0 | 0.0 | 198.3 | 122.8 | 197.8 | 122.5 |
| DRY TIME MINUTES | 55 | 50 | 45 | 30 | 50 | 25 | 25 | 45 |

Figure 5:
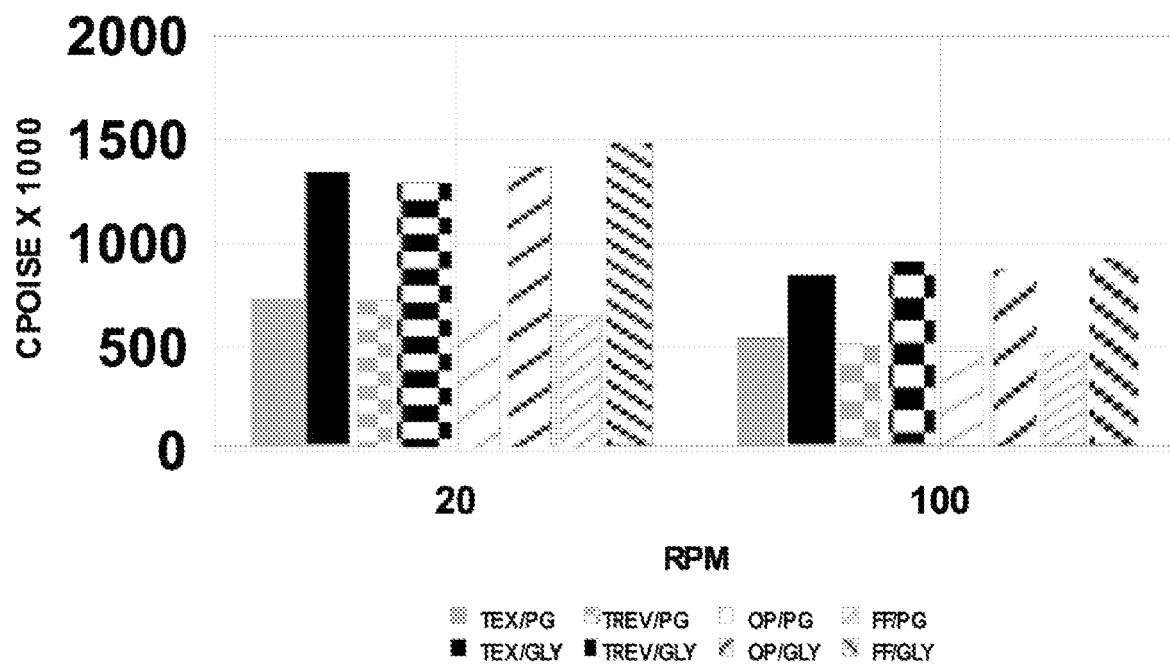
FIG. 5 is a bar graph showing the viscosity at 20 rpm and 100 rpm in a Styrene Acrylic Semi Gloss formula.

FIG. 5 shows the viscosity results (styrene acrylic semi gloss) in graphical form.

Example 10

Acrylic Semi Gloss Formula

Bis(2-ButoxyEthyl Carbonate) was tested in a number of water-based flat paints, as set out in Example 3. Table 17 shows materials and combinations tested in an acrylic semi gloss formula.

TABLE 17

| | FORMULATION ACRYLIC SEMI-GLOSS | | | | | | | |
|---|---|---|---|---|---|---|---|---|
| | A | B | C | D | E | F | G | H |
| WATER | | | | 223.0 | | | | |
| AMP-95 | | | | 3.2 | | | | |
| COLLOIDS 226 | | | | 8.0 | | | | |
| COLLIDS 691 | | | | 4.0 | | | | |
| TIO2(R-706) | | | | 152.0 | | | | |
| HUBERCARB 3G | | | | 78.0 | | | | |
| ERCOR 662 | | | | 530.0 | | | | |
| ACRYSOL TT-935 | | | | 10.0 | | | | |
| AMMONIA | | | | 10.0 | | | | |
| TEXANOL | 8.3 | 8.3 | | | | | | |
| TREVISOL | | | 8.3 | 8.3 | | | | |
| OPTIFILM 400 | | | | | 8.3 | 8.3 | | |
| UCAR FILM IBT | | | | | | | 8.3 | 8.3 |
| PROPYLENE GLYCOL | 20.0 | | 20.0 | | 20.0 | | 20.0 | |
| GLYKOSOL | | 20.0 | | 20.0 | | 20.0 | | 20.0 |

The results for the viscosities (acrylic semi gloss) are shown in Table 18.

TABLE 18

| CQ217018 ACRYLIC SEMIGLOSS | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 12400 | 7200 | 3840 | 2400 | 1520 | 990 | 600 | 422 | 600 | 1000 | 1520 | 2400 | 3760 | 6800 | 11600 |
| TEX/GLY | 8800 | 6400 | 4160 | 2920 | 2200 | 1720 | 1280 | 1018 | 1272 | 1680 | 2100 | 2760 | 3760 | 5800 | 7600 |
| TREV/PG | 11600 | 6600 | 3520 | 2240 | 1480 | 1000 | 644 | 482 | 640 | 980 | 1420 | 2120 | 3280 | 6000 | 10000 |
| TREV/GLY | 6000 | 5200 | 5760 | 3640 | 3080 | 2670 | 2156 | 1700 | 2156 | 2660 | 3060 | 3560 | 4240 | 6200 | 6800 |
| OP/PG | 9600 | 6600 | 3520 | 2240 | 1480 | 1000 | 636 | 476 | 636 | 980 | 1420 | 2160 | 3360 | 6200 | 10000 |
| OP/GLY | 5600 | 5000 | 3920 | 3200 | 2620 | 2220 | 1764 | 1418 | 1764 | 2190 | 2580 | 3080 | 3840 | 4800 | 5600 |
| FF/PG | 11200 | 7000 | 3760 | 2320 | 1500 | 980 | 596 | 426 | 596 | 970 | 1460 | 2280 | 3680 | 7000 | 11600 |
| FF/GLY | 7200 | 6400 | 4160 | 3000 | 2260 | 1770 | 1324 | 1056 | 1316 | 1730 | 2180 | 2880 | 3840 | 6000 | 8400 |

The results for different parameters (acrylic semi gloss) are shown in Table 19.

TABLE 19

| | TEX PG CONTROL | TEX GLY | TREV PG | TREV GLY | OP PG | OP GLY | FF PG | FF GLY |
|---|---|---|---|---|---|---|---|---|
| 20 Deg Gloss | 6.9 | 6.7 | 6.8 | 6.8 | 7.1 | 7.2 | 7.2 | 6.9 |
| 60 Deg Gloss | 30.4 | 29.4 | 29.7 | 29.7 | 30.5 | 30.4 | 30.9 | 30.5 |
| L* | 96.1 | 96.6 | 96.6 | 96.8 | 96.6 | 96.7 | 96.7 | 96.7 |
| a* | −0.8 | −0.8 | −0.8 | −0.8 | −0.8 | −0.7 | −0.8 | −0.8 |
| b* | 0.8 | 0.8 | 0.8 | 1 | 0.9 | 0.9 | 0.9 | 0.9 |
| Opacity (Y) | 93.7 | 94.3 | 93.7 | 94.1 | 94.1 | 94.3 | 93.8 | 94.2 |
| VOC (CALCULATED) | 133.6 | 43.1 | 98.8 | 0.0 | 134.1 | 43.3 | 134.0 | 43.2 |
| DRY TIME MINUTES | 15 | 20 | 25 | 30 | 20 | 30 | 25 | 30 |

Figure 6A:
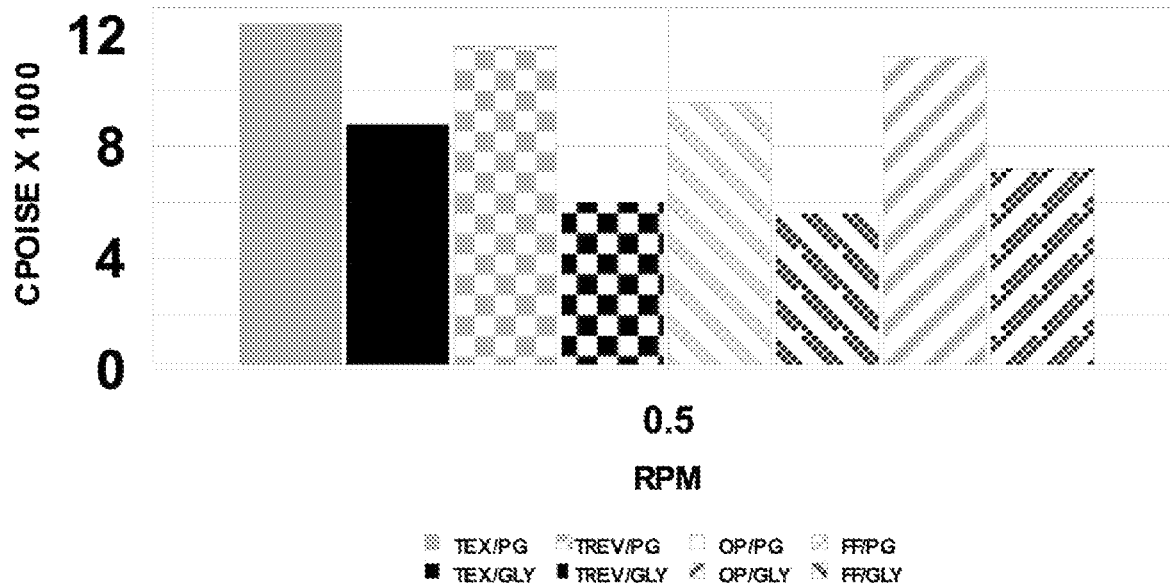
FIG. 6A is a bar graph showing the viscosity at 0.5 rpm, #4 spindle, in an Acrylic Semi Gloss formula.
Figure 6B:
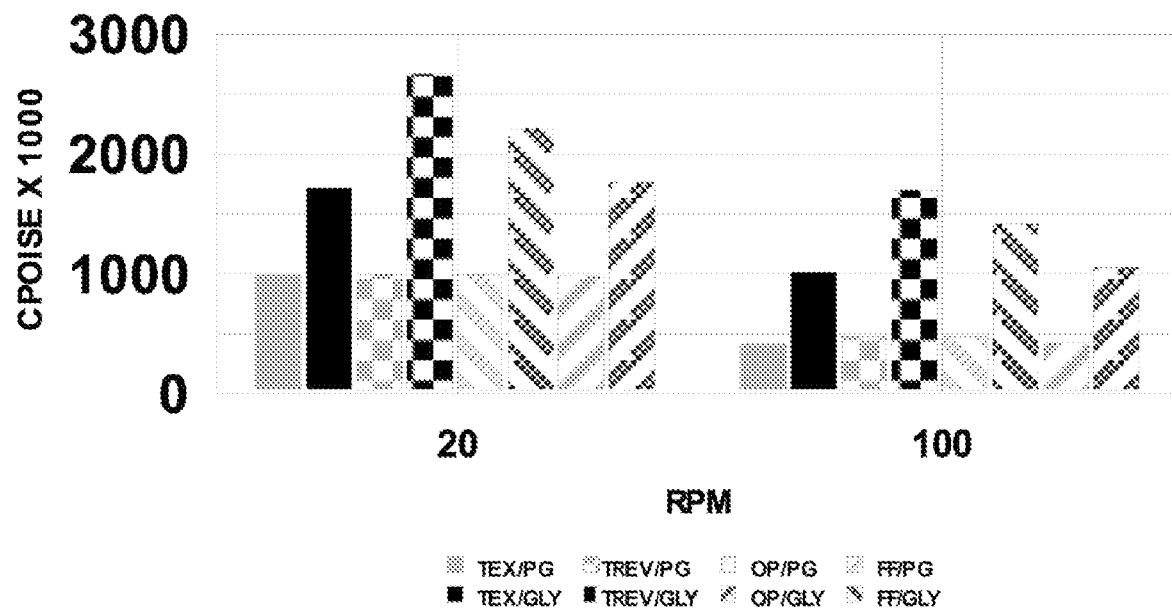
FIG. 6B is a bar graph showing the viscosity at 20 rpm and 100 rpm, #4 spindle, in an Acrylic Semi Gloss formula.
Figure 6C:
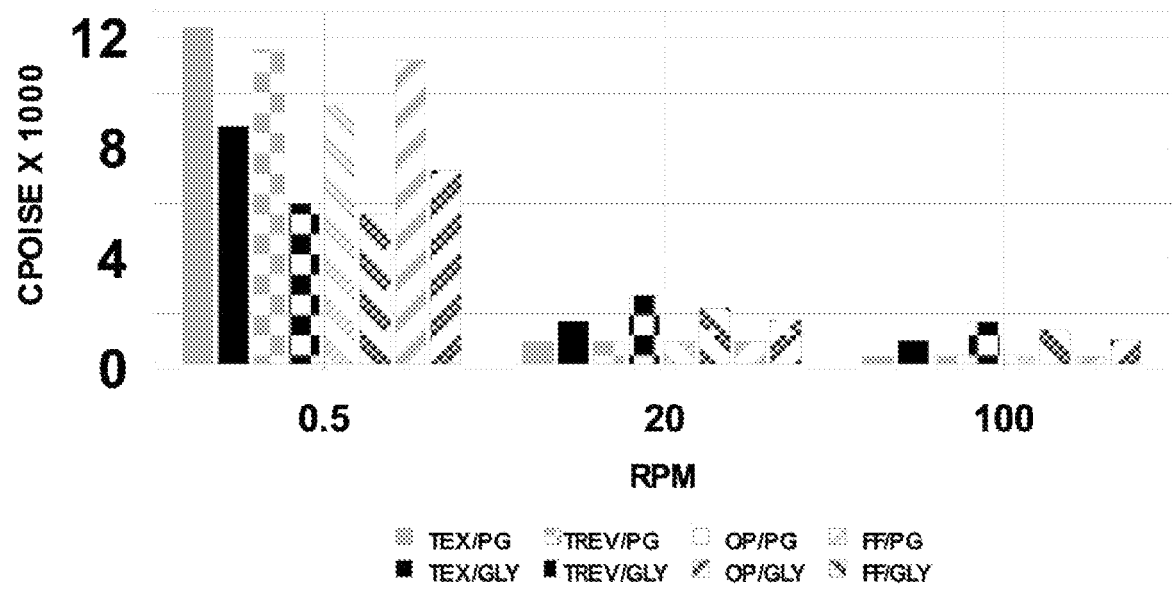
FIG. 6C is a bar graph showing the viscosity at 0.5 rpm, 20 rpm and 100 rpm, #4 spindle, in an Acrylic Semi Gloss formula.

FIGS. 6A-C show the viscosity results (acrylic semi gloss) in graphical form, where TEX is Texanol™, PG is Propylene Glycol, GLY is GlykoSol, OP is Optifilm™ 400, and FF is Film Former IBT.

Example 11

Acrylic Flat Formula

Bis(2-ButoxyEthyl Carbonate) was tested in a number of water-based flat paints, as set out in Example 3.

The results for the viscosities (acrylic flat) are shown in Table 20.

TABLE 20

| CQ218002 ACRYLIC FLAT | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 1400 | 1300 | 1240 | 1000 | 840 | 715 | 596 | 542 | 624 | 735 | 820 | 900 | 1000 | 1200 | 1400 |
| TEX/GLY | 3800 | 3800 | 3000 | 2240 | 1720 | 1345 | 1020 | 842 | 1004 | 1240 | 1440 | 1660 | 1920 | 2200 | 2800 |
| TREV/PG | 1600 | 1500 | 1320 | 1040 | 860 | 725 | 586 | 508 | 588 | 700 | 780 | 840 | 960 | 1200 | 1200 |
| TREV/GLY | 2800 | 2800 | 2360 | 1940 | 1580 | 1295 | 1080 | 907 | 1088 | 1355 | 1560 | 1800 | 2040 | 2400 | 2800 |
| OP/PG | 1200 | 1300 | 1200 | 940 | 790 | 665 | 542 | 479 | 548 | 640 | 720 | 780 | 880 | 1000 | 1200 |
| OP/GLY | 4800 | 4100 | 2760 | 2160 | 1720 | 1375 | 1050 | 867 | 1046 | 1320 | 1550 | 1800 | 2080 | 2500 | 2800 |
| FF/PG | 1400 | 1300 | 1080 | 920 | 760 | 650 | 540 | 478 | 544 | 635 | 700 | 760 | 880 | 900 | 1000 |
| FF/GLY | 4400 | 4200 | 3280 | 2500 | 1890 | 1485 | 1122 | 922 | 1108 | 1395 | 1630 | 1900 | 2200 | 2600 | 3000 |

Figure 7A:
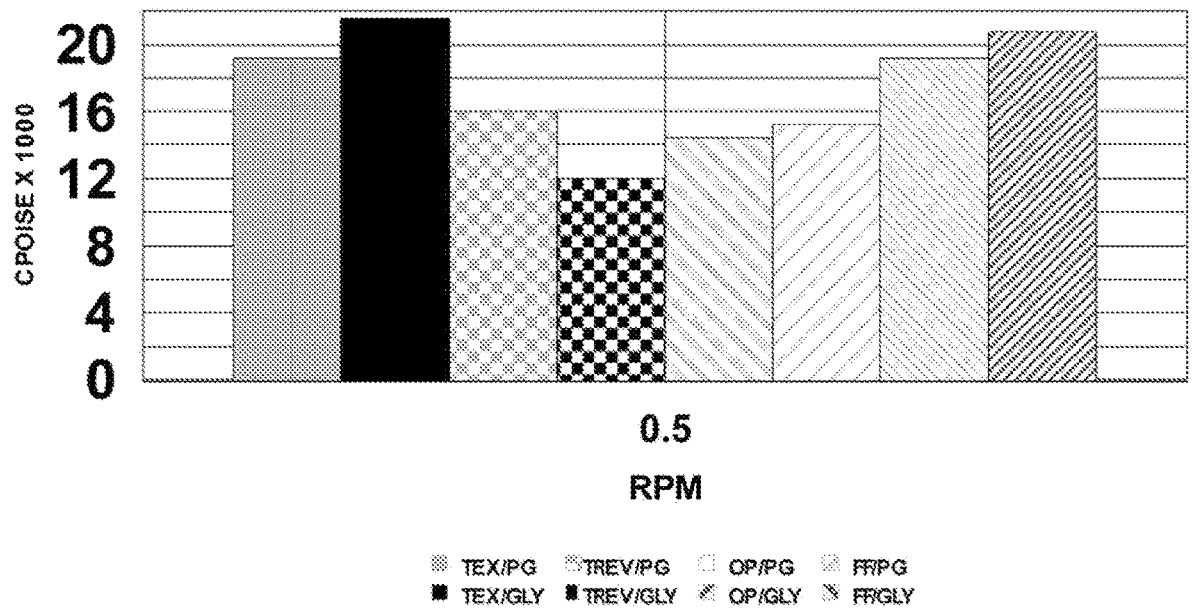
FIG. 7A is a bar graph showing the viscosity at 0.5 rpm, #5 spindle, in an Acrylic Flat formula.
Figure 7B:
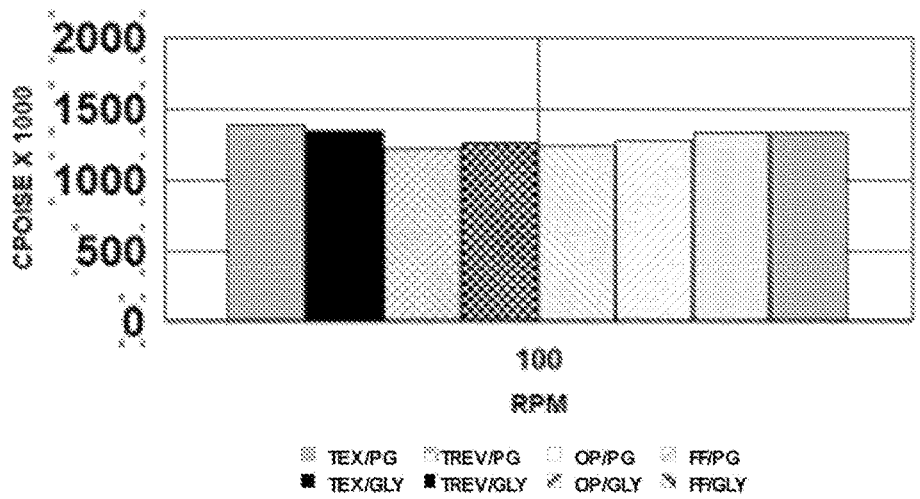
FIG. 7B is a bar graph showing the viscosity at 100 rpm, #5 spindle, in an Acrylic Flat formula.
Figure 7C:
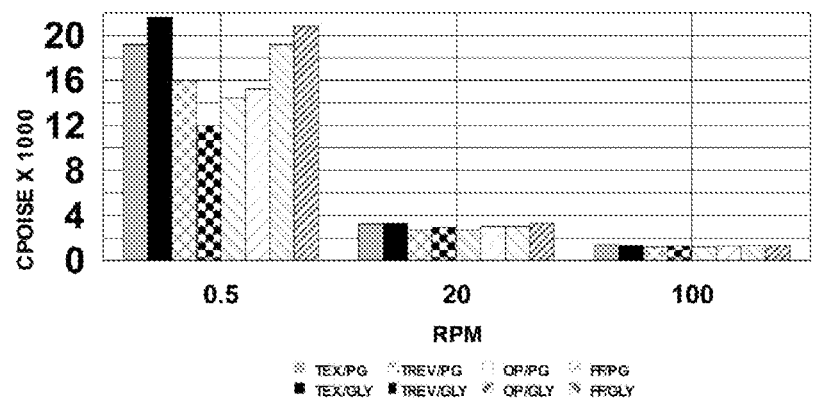
FIG. 7C is a bar graph showing the viscosity at 0.5 rpm, 20 rpm and 100 rpm, #5 spindle, in an Acrylic Flat formula.

FIGS. 7A-C show the viscosity results (acrylic flat) in graphical form.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined by the claims appended hereto.

What is claimed is:

1. A method of reducing an amount of volatile organic components in a composition, the method comprising:
   replacing at least a portion of a glycol ether, or an alkyl ether of diethylene glycol, ethylene glycol or propylene glycol in the composition with a compound of Formula (I):

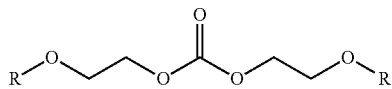

Formula (I)

wherein R is $C_{1-12}$ alkyl, optionally substituted from one up to the maximum number of substituents with oxygen.

2. The method of claim 1, wherein the replacing comprises replacing a glycol ether with the compound of Formula (I).

3. The method of claim 1, wherein the replacing comprises replacing a propylene glycol with the compound of Formula (I).

4. The method of claim 1, wherein the compound of Formula (I) is:

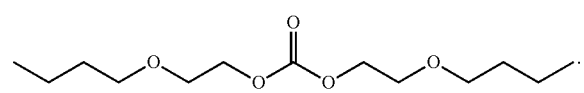

5. The method of claim 1, wherein the compound of Formula (I) is:

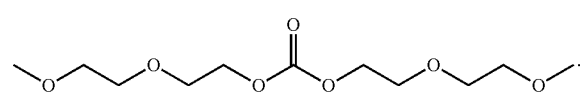

6. The method of claim 1, wherein the composition comprises a paint, coating or oil dispersant.

7. The method of claim 1, wherein the composition comprises a pharmaceutical, nutritional, dietary or cosmetic product, and the compound of Formula (I) is an excipient.

8. The method of claim 1, wherein the compound of Formula (I) is a carrier of an active ingredient in the composition.

9. The method of claim 1, wherein the composition is a cleaning solvent, a reactive solvent, co-solvent, dispersant, wetting agent, coupling agent, stabilizer, chemical intermediate, coalescent, or viscosity reduction solvent.

10. The method of claim 1, wherein the compound of Formula (I) is a coupling agent in the composition.

11. The method of claim 1, wherein the compound of Formula (I) is a solvent, co-solvent or coalescent, and the composition is a water borne alkyd, conventional lacquer, dye, stain, latex, acrylic, alkyd, architectural paint and/or coatings formulation.

12. The method of claim 1, wherein the composition is a cleaning and/or degreasing formulation, and the composition further comprises a surfactant.

13. The method of claim 1, wherein the compound of Formula (I) is an intermediate in a chemical reaction.

14. The method of claim 2, wherein the compound of Formula (I) is:

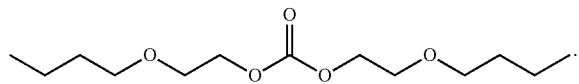 [SMILES: CCCCOCCOC(=O)OCCOCCCC]

15. The method of claim 2, wherein the compound of Formula (I) is:

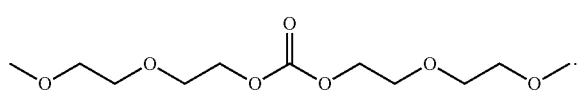

16. The method of claim 3, wherein the compound of Formula (I) is:

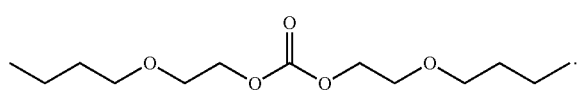 [SMILES: CCCCOCCOC(=O)OCCOCCCC]

17. The method of claim 3, wherein the compound of Formula (I) is:

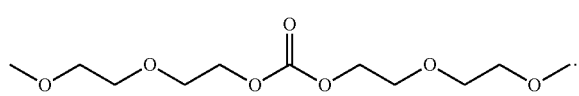

18. The method of claim 9, wherein the compound of Formula (I) is:

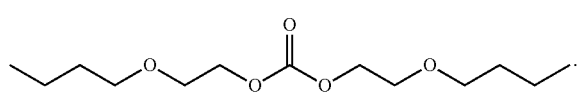 [SMILES: CCCCOCCOC(=O)OCCOCCCC]

19. The method of claim 9, wherein the compound of Formula (I) is:

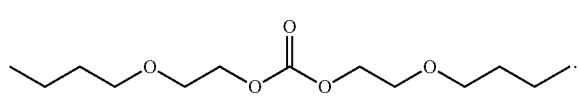 [SMILES: CCCCOCCOC(=O)OCCOCCCC]

* * * * *

UNITED STATES PATENT AND TRADEMARK OFFICE
CERTIFICATE OF CORRECTION

PATENT NO. : 10,975,016 B2  
APPLICATION NO. : 16/652956  
DATED : April 13, 2021  
INVENTOR(S) : David A. Pasin et al.

Page 1 of 1

It is certified that error appears in the above-identified patent and that said Letters Patent is hereby corrected as shown below:

In the Claims

In Claim 19, delete "  ." and insert 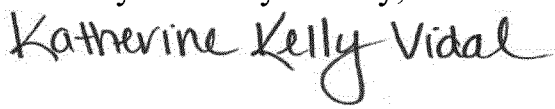 .--

Signed and Sealed this  
Thirty-first Day of May, 2022

*Katherine Kelly Vidal*

Katherine Kelly Vidal  
*Director of the United States Patent and Trademark Office*